(12) United States Patent
Shimada et al.

(10) Patent No.: US 12,403,045 B2
(45) Date of Patent: Sep. 2, 2025

(54) MANUFACTURING APPARATUS AND METHOD FOR ABSORBENT BODY

(71) Applicant: ZUIKO CORPORATION, Osaka (JP)

(72) Inventors: Takahiro Shimada, Osaka (JP); Kazuma Nagata, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 647 days.

(21) Appl. No.: 17/625,117

(22) PCT Filed: Jul. 10, 2020

(86) PCT No.: PCT/JP2020/026979
§ 371 (c)(1),
(2) Date: Jan. 6, 2022

(87) PCT Pub. No.: WO2021/015001
PCT Pub. Date: Jan. 28, 2021

(65) Prior Publication Data
US 2022/0265483 A1    Aug. 25, 2022

(30) Foreign Application Priority Data

Jul. 23, 2019 (JP) .................................. 2019-135217

(51) Int. Cl.
*A61F 13/537* (2006.01)
*A61F 13/15* (2006.01)

(52) U.S. Cl.
CPC .. *A61F 13/15658* (2013.01); *A61F 13/15699* (2013.01); *A61F 13/15764* (2013.01); *A61F 13/537* (2013.01); *A61F 2013/15821* (2013.01)

(58) Field of Classification Search
CPC .......... A61F 13/15658; A61F 13/15699; A61F 13/15754; A61F 13/537; A51F 2013/15821
(Continued)

(56) References Cited

U.S. PATENT DOCUMENTS

| 2016/0175169 A1 | 6/2016 | Bianchi |
| 2017/0095379 A1 | 4/2017 | Cipriani |
| 2019/0029890 A1 | 1/2019 | Nakamura |

FOREIGN PATENT DOCUMENTS

| JP | 9-266929 A | 10/1997 |
| JP | 2017-99855 A | 6/2017 |

(Continued)

OTHER PUBLICATIONS

International Search Report for corresponding Application No. PCT/JP2020/026979, mailed Oct. 13, 2020.

*Primary Examiner* — Christina A Johnson
*Assistant Examiner* — Xue H Liu
(74) *Attorney, Agent, or Firm* — Renner, Otto, Boisselle & Sklar, LLP

(57) ABSTRACT

A manufacturing apparatus for an absorbent body including: a first conveyor that conveys an air-permeable first sheet while sucking the first sheet along a flat first slope surface; a second conveyor that conveys an air-permeable second sheet while sucking the second sheet along a flat second slope surface having a slope opposite to the first slope surface; a first distribution device that forms a first absorbent layer in the first sheet by distributing absorbent powder on an upper surface of the first sheet being conveyed along the first slope surface; a second distribution device that forms a second absorbent layer in the second sheet by distributing absorbent powder on an upper surface of the second sheet being conveyed along the second slope surface; and a stacking part that stacks the first sheet conveyed by the first conveyor and the second sheet conveyed by the second conveyor in such a manner as to cause the first absorbent layer of the first sheet and the second absorbent layer of the second sheet to face each other.

5 Claims, 6 Drawing Sheets

(58) Field of Classification Search
USPC .......................................................... 425/81.1
See application file for complete search history.

(56) References Cited

FOREIGN PATENT DOCUMENTS

| | | |
|---|---|---|
| JP | 2018-502627 A | 2/2018 |
| JP | 3218416 U | 10/2018 |
| WO | 2015/123087 A1 | 8/2015 |
| WO | 2017/131014 A1 | 8/2017 |

MANUFACTURING APPARATUS AND METHOD FOR ABSORBENT BODY

TECHNICAL FIELD

The present invention is related to manufacturing apparatus and method for an absorbent body having super absorbent particle polymer in its fluffed-up sheet.

BACKGROUND ART

Such type of the apparatus and method have been known in the art. (Patent document 1 below) In the invention disclosed in the document 1, the first absorbent layer is formed by sprinkling the absorbent granular powder to one-side surface of the first sheet conveyed by the first drum and keeping the powder in the surface; the second absorbent layer is formed by sprinkling the granular powder to one-side surface of the second sheet conveyed by the second drum and keeping the powder in the surface; and the surfaces of the first and second sheets having the granular powder therein are faced and stacked with each other, thereby the absorbent body formed.

CITATION LIST

Patent Document

Patent document 1: WO2015/123087

SUMMARY OF INVENTION

However, as the granular powder is sprinkled on the cylindrical surface of the drum, centrifugal force generates to each absorbent layer along the cylindrical surface. Thus, the granular powder is likely to scatter around the apparatus.

The object of the present invention is to prevent absorbent granular powder from scattered in manufacturing apparatus and method for an absorbent body.

A manufacturing apparatus of the present invention includes:
- a first conveyor C1 that conveys an air-permeable first sheet S1 while sucking the first sheet S1 along a flat first slope surface F1;
- a second conveyor C2 that conveys an air-permeable second sheet S2 while sucking the second sheet S2 along a flat second slope surface F2 having a slope opposite to the first slope surface F1;
- a first distribution device 11 that forms a first absorbent layer L1 in the first sheet S1 by distributing absorbent powder on an upper surface of the first sheet S1 being conveyed along the first slope surface F1;
- a second distribution device 12 that forms a second absorbent layer L2 in the second sheet S2 by distributing absorbent powder on an upper surface of the second sheet S2 being conveyed along the second slope surface F2; and
- a stacking part that stacks the first sheet S1 conveyed by the first conveyor C1 and the second sheet S2 conveyed by the second conveyor C2 in such a manner as to cause the first absorbent layer L1 of the first sheet S1 and the second absorbent layer L2 of the second sheet S2 to face each other.

Meanwhile, the method of the present invention includes:
- a step of conveying the first and second sheets S1 and S2 toward the stacking part while sucking the first sheet S1 and the second sheet S2 along the flat first slope surface of the first conveyor C1 and the flat second slope surface of the second conveyor C2 respectively;
- a step of distributing the powder on the upper surfaces of the first and second sheets S1 and S2 extending along the respective flat slope surfaces;
- a step of forming the first and second absorbent layers L1 and L2 by supporting the distributed powder on the first and second sheets S1 and S2; and
- a step of stacking the first sheet S1 and the second sheet S2 in such a manner as to cause the first absorbent layer L1 and the second absorbent layer L2 to face each other at the stacking part.

In the present invention, the first and second slope surfaces are not curved cylindrical surfaces, but flat surfaces. Thus, the granular powder does not scatter around even centrifugal force is generated. Also, centrifugal force does not generate in the granular powder not sucked by the corresponding conveyor. Thus, such granular powder drops toward the stacking part of both absorbent layers, and is held between the absorbent layers without scattered around.

DESCRIPTION OF EMBODIMENTS

Figure 1:
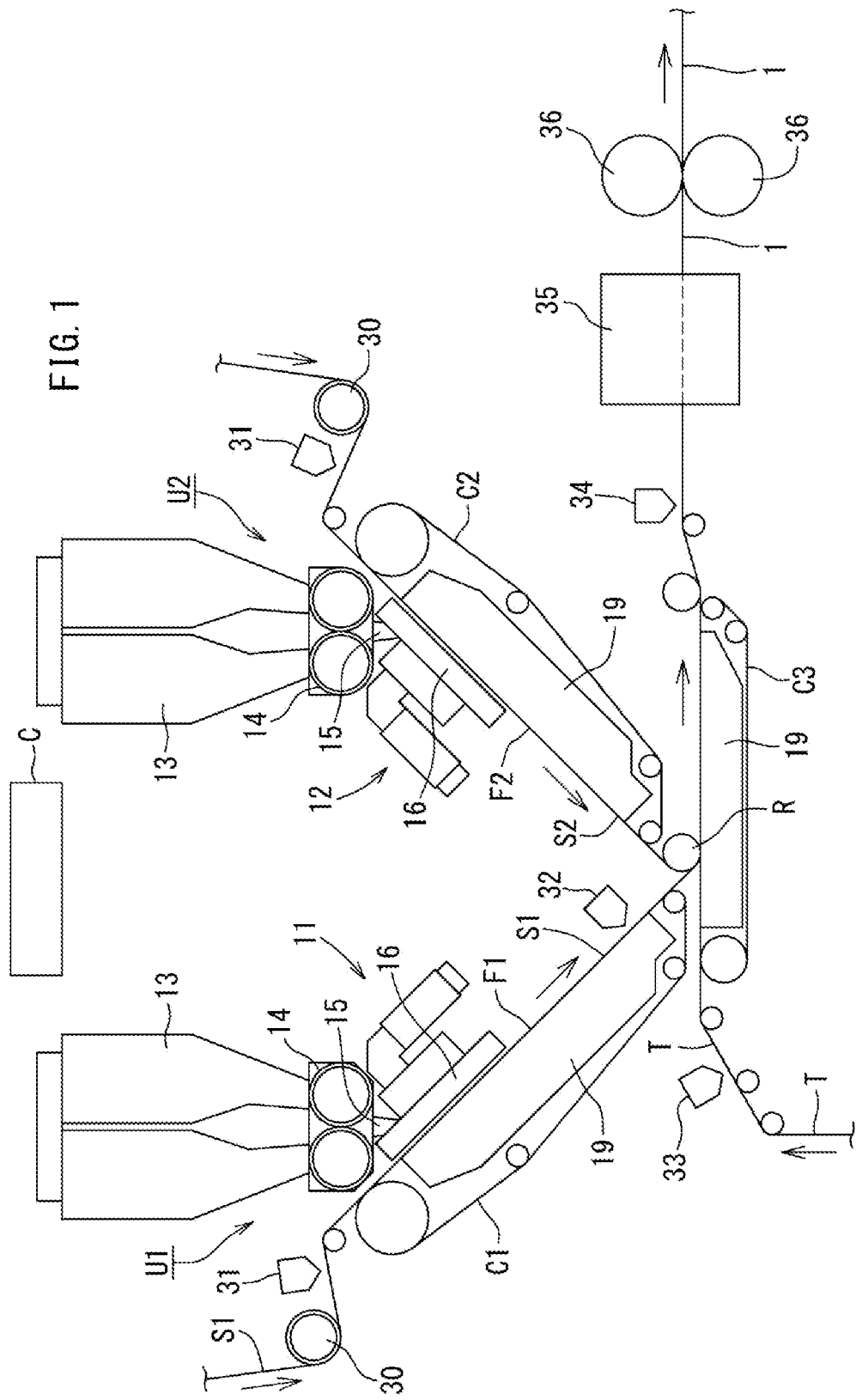
FIG. 1 is a schematic layout diagram showing an embodiment 1 of the manufacturing apparatus of the present invention.

In a preferred apparatus, the stacking part is a stacking roller R that rolls in the first sheet S1 conveyed by the first conveyor C1 and the second sheet S2 conveyed by the second conveyor C2 and also stacks the first sheet S1 and the second sheet S2 on each other.

In this case, it is easy to stack the first sheet and the second sheet.

More preferably, the first conveyor C1, the second conveyor C2, and the stacking roller R are arranged in such a manner that the upper surfaces of the first and second sheets S1 and S2 conveyed by the first conveyor C1, the second conveyor C2, and the stacking roller R form a V-shape valley.

In a case where both conveyors and the stacking roller R form a V-shape valley aforementioned, granular powder not held on the surface of each sheet is to be sandwiched between the two absorbent layers.

Another preferred apparatus further includes an introduction part 50 that introduces a liquid-permeable third sheet S3 to be interposed between the first sheet S1 and the second sheet S2 into the stacking roller R.

In this case, the third sheet is provided between the two sheets. Thus, it is possible to prevent gel block—granular powder held in the first and second sheets are joined together—from occurring.

Another preferred apparatus further includes a controller C that selectively controls operation of at least one of a first unit U1 including the first conveyor C1 and the first distribution device 11 and a second unit U2 including the second conveyor C2 and the second distribution device 12.

In this case, it is possible to manufacture absorbent bodies having different thickness and shapes as described later.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Prior to an explanation of the present manufacturing apparatus, one example of an absorbent body manufactured by the present manufacturing apparatus is explained first.

Figure 3:
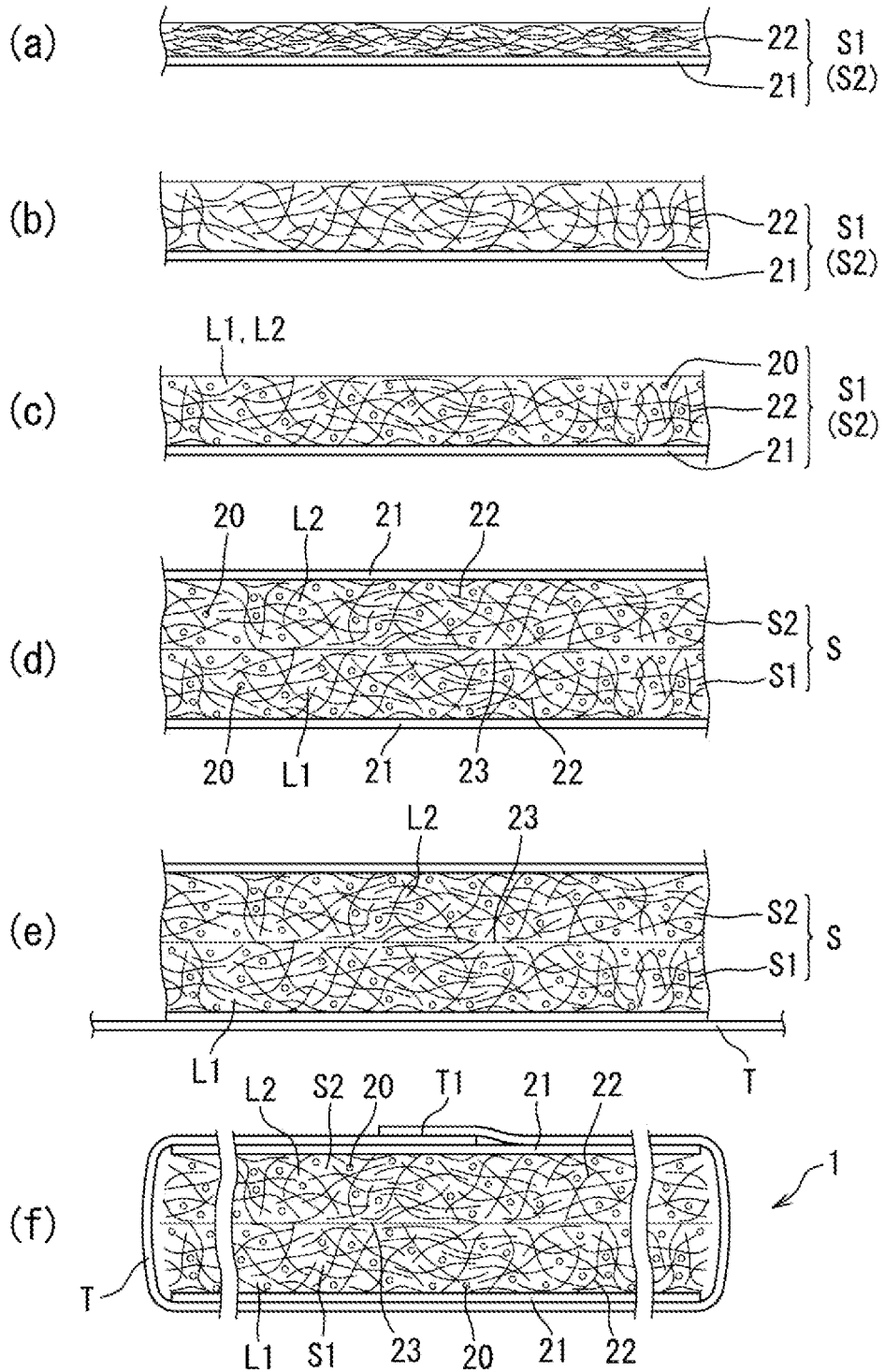
FIG. 3 is an enlarged cross-sectional view showing manufacturing process of an absorbent body.

FIG. 3 is an enlarged cross-sectional view showing an absorbent body as well as its manufacturing steps. FIG. 3 (f) shows an absorbent body 1 used as an absorbent core for a disposable diaper, for example.

As shown in FIG. 3 (f), an absorbent body 1 includes: a first sheet S1 and a second sheet S2 each having granular powder 20; and a thin paper (tissue paper) T wrapping the first sheet S1 and the second sheet S2.

In FIG. 3 (a), the first and second sheets S1, S2 are not yet fluffed up (i.e., before raising). In this FIG., a spread layer 21 at the back side as a base and a short fiber layer 22 at the front side are stacked.

The short fiber layer 22 is a non-woven fabric layer formed from short fiber, and is formed by the air blow process, for example. Such non-woven fabric layer may be formed by blowing hot air on lined-up short fiber.

On the other hand, the spread layer 21 is thinner than the short fiber layer 22 and has higher density than the short fiber layer 22. The spread layer 21 allows liquid to permeate across an extensive area due to its high diffusibility in the planar direction.

In FIG. 3 (b), the first and second sheets S1, S2 are fluffed up. The first and second sheets S1, S2 transform from a state where the short fiber layer 22 lies (not fluffed-up) to a state where the short fiber layer 22 is raised to have small bulk density and to become thick.

As shown in FIG. 3 (c), the short fiber layer 22 of the first and second sheet S1, S2 after raising is in a state where the granular powder 20 is sprinkled. The granular powder 20 is well-known superabsorbent polymer (SAP). The short fiber layer 22 holding the granular powder 20 configures a first absorbent layer L1 and a second absorbent layer L2.

As shown in FIG. 3 (d), the first and second sheets S1, S2 including the granular powder 20 are stacked together such that the short fiber layers 22 of both sheets contact with each other with an adhesion layer 23 therebetween, thereby becoming one-sheet thick stack S. In this state, the first and second absorbent layers L1, L2 face and contact each other.

As shown in FIG. 3 (e)-(f), the stack S is wrapped by the thin paper T, becoming a well-known absorbent body 1.

Now, embodiments of the manufacturing apparatus by the present invention are explained with reference to the drawings.

Figure 2:
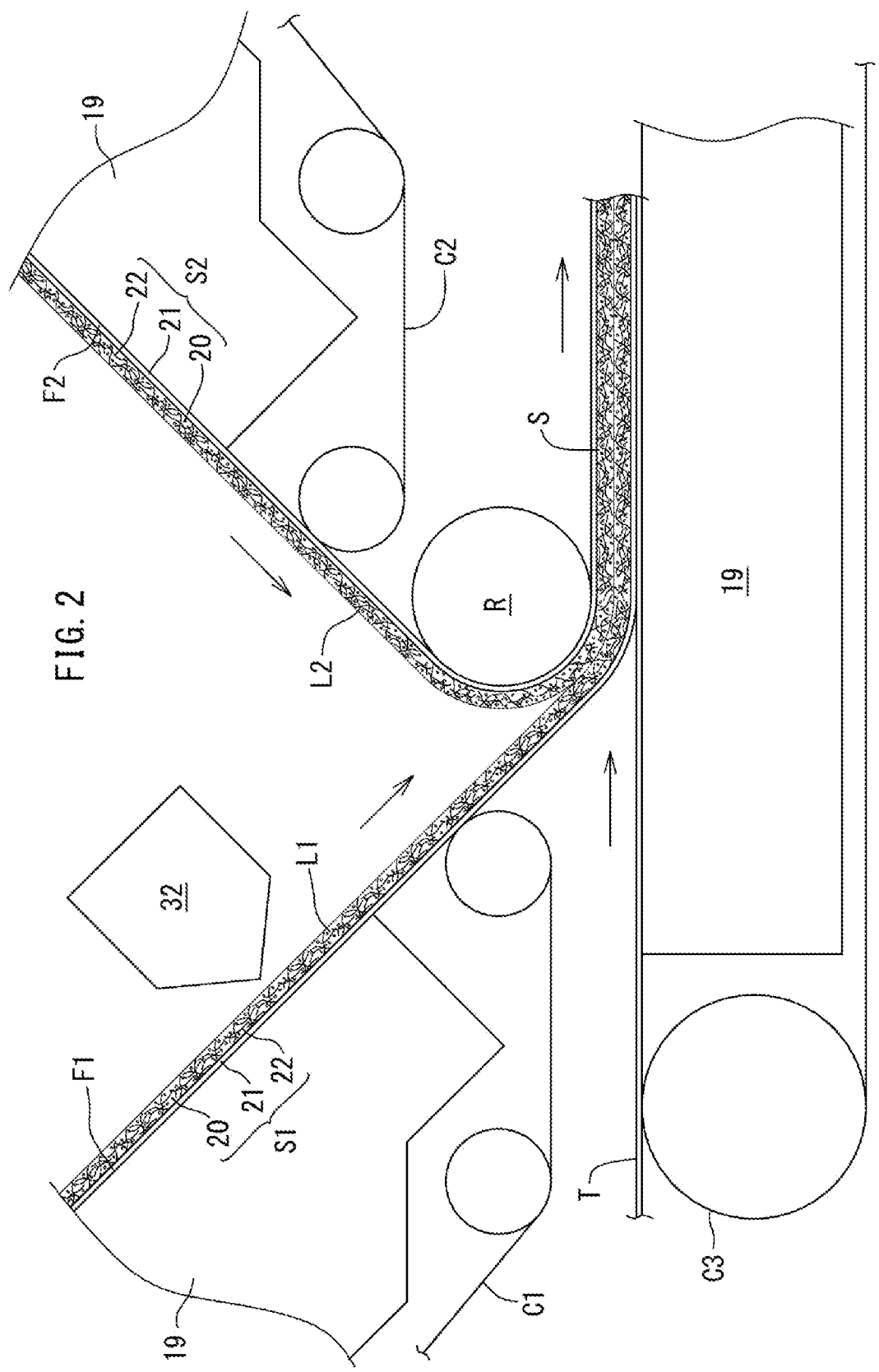
FIG. 2 is a side view showing an enlarged stacking part.

FIG. 1 and FIG. 2 shows an embodiment 1.

As shown in FIG. 1, the present manufacturing apparatus includes a first unit U1, a second unit U2, a stacking roller R (one example of stacking part), and a controller C. The first and second units U1, U2 have a similar structure, and are arranged in reflection symmetry (plane symmetry).

The first unit U1 includes a first conveyor C1 and a first distribution device 11. The second unit U2 includes a second conveyor C2 and a second distribution device 12. The controller C selectively controls at least one of the first and second units U1, U2.

The first conveyor C1 conveys an air-permeable first sheet S1 along a flat first slope surface F1 while sucking the first sheet S1. The second conveyor C2 conveys an air-permeable second sheet S2 along a flat second slope surface F2 tilting opposite to the first slope surface F1 while sucking the second sheet S2. As described later, top surfaces (upper surfaces) of the first and second sheets S1, S2 are fluffed up (raised) in advance.

The first distribution device 11 sprinkles absorbent granular powder on the upper surface of the first sheet S1 conveyed along the first slope surface F1, forming the first absorbent layer L1 in the short fiber layer 22 of the first sheet S1 of FIG. 2. The second distribution device 12 of FIG. 1 sprinkles absorbent granular powder on the upper surface of the second sheet S2 conveyed along the second slope surface F2, forming the second absorbent layer L2 in the short fiber layer 22 of the second sheet S2 of FIG. 2. After sprinkled, the granular powder 20 gets into each short fiber layer (absorbent layer) 22 by negative pressure from a corresponding negative pressure case 19 while the first and second sheets S1, S2 are conveyed by the first and second conveyors C1, C2, respectively.

In FIG. 2, the stacking roller R stacks the first and second sheets S1, S2 so that the first absorbent layer L1 of the first sheet S1 conveyed by the first conveyor C1 and the second absorbent layer L2 of the second sheet S2 conveyed by the second conveyor C2 face each other. In other words, the stacking roller R rolls in the first sheet S1 conveyed by the first conveyor C1 and the second sheet S2 conveyed by the second conveyor C2, and puts them together.

The first conveyor C1, the second conveyor C2 and the stacking roller R are arranged so that the upper surfaces of the first and second sheets S1, S2 conveyed by the first conveyor C1, the second conveyor C2 and the stacking roller R of FIG. 1 form a V-shaped valley.

Now, feeding the first and second sheets S1, S2 is described.

As shown in FIG. 1, the first and second sheets S1, S2 are fed to a corresponding fluff-up roller 30, and then are conveyed by the respective first and second conveyors C1, C2. At the stacking roller R, the first and second sheets S1, S2 are joined and stacked together. As described later, each conveyor C1, C2 of FIG. 2 is provided with a negative pressure case 19 that sucks a corresponding sheet during conveyance to hold the granular powder 20 in the short fiber layer 22 of the sheet.

The fluff-up roller 30 of FIG. 1 is a roller having a lot of teeth and rotates slower than the conveyance speed of the sheets S1, S2. With this speed difference, the fluff-up roller 30 raises (fluffs up) the short fiber layer 22 of the sheet of FIG. 3 (a) as shown in FIG. 3 (b).

The first applicator 31 for adhesive is provided between the fluff-up roller 30 and the conveyors C1, C2 of FIG. 1. Adhesive is applied to the front surface of the raised short fiber layer 22 (FIG. 3 (b)).

Now, sprinkling of the granular powder 20 of FIG. 1 is explained.

A first distribution device 11 and a second distribution device 12 sprinkle the granular powder 20 on the sheet. Each device includes a hopper 13 storing the granular powder 20, a meter 14, a guider 15 and a distribution case 16. The distribution case 16 is provided with a distribution mouth and a shutter for opening/closing the distribution mouth. With this configuration, a predetermined granular powder 20 is sprinkled intermittently on the short fiber layer 22 (FIG. 2) of the corresponding sheet.

Feeding of sheets and sprinkling of the granular powder are disclosed in WO2017/131014, for example, and its disclosure is incorporated herein by reference.

Now, steps of stacking the sheets S1, S2 and thereafter are explained.

As shown in FIG. 2, the second applicator 32 applies adhesive to the sheet S1 of the sheets, which the granular powder 20 is sprinkled. With this application, the short fiber layers 22 of the first and second sheets S1, S2 are joined together after the sheets S1, S2 are stacked by the stacking roller R.

In FIG. 1, a thin paper T is fed on the stacking conveyor C3. The third applicator 33 is provided upstream of the stacking conveyor C3, and applies adhesive to the center area of the upper surface of the thin paper T.

As shown in FIG. 2, the stacking conveyor C3 conveys the sheet material downstream in a state where the thin paper T is provided under the stack S of the first and second sheets S1, S2 stacked together. In the conveyance, the stack S is joined to the front surface of the thin paper T. In the present embodiment, the stacking conveyor C3 contacts the stacking roller R with the stack S and the thin paper T therebetween.

The fourth applicator 34, a folder 35 and a pair of pressure contact rollers 36 are provided downstream of the stacking conveyor C3 of FIG. 1. Note that the stacking conveyor C3 includes a negative pressure case 19 sucking the thin paper T.

The fourth applicator 34 applies adhesive to side edges of the upper surface of the thin paper T. Note that a width of the thin paper T is more than two times larger than that of the stack S.

The folder 35 of FIG. 1 folds the thin paper T as shown in FIG. 3 (f) to wrap the stack S by the thin paper T, forming the absorbent body 1. The pressure contact roller 36 presses hard the absorbent body 1 in its thickness direction.

Now, a method of manufacturing the absorbent body 1 having the first sheet S1 and the second sheet S2 of FIG. 3 (f) is explained. In this case where the first and second sheets are used, both first and second units U1, U2 of FIG. 1 are operated.

The first sheet S1 and the second sheet S2 are fed to the corresponding fluff-up roller 30,30, and the short fiber layer 22 of FIG. 3 (a) of each sheet is raised (fluffed up). Then, the first applicator 31 (FIG. 1) applies adhesive to the raised short fiber layer 22 of FIG. 3 (b). Thereafter, the first and second sheets S1, S2 of FIG. 1 are conveyed toward the stacking roller R along the flat slope surface of the respective first and second conveyors C1, C2 while the sheets S1, S2 are sucked by the first and second conveyors C1, C2.

Granular powder is sprinkled on the upper surfaces of the first and second sheets S1, S2 of FIG. 1 along their flat slope surfaces. The first distribution device 11 and the second distribution device 12 sprinkle the granular powder 20 on the respective first and second sheet S1, S2, forming the first absorbent layer L1 and the second absorbent layer L2 (FIG. 3 (c)) of FIG. 2 including the granular powder 20. In other words, the sprinkled granular powder 20 is held in the short fiber layer 22 of the first and second sheets S1, S2, thereby the first and second absorbent layers L1, L2 formed.

In detail, after sprinkled, the granular powder 20 gets into the short fiber layer (absorbent layer) 22 of each first and second sheet S1, S2 by the negative pressure from the corresponding negative pressure case 19 while the first and second sheets S1, S2 are conveyed by the first and second conveyors C1, C2.

Thereafter, the first sheet S1 and the second sheet S2 are stacked together at the stacking roller R so that the first absorbent layer L1 and the second absorbent layer L2 face each other. In other words, the first absorbent layer L1 of the first sheet S1 and the second absorbent layer L2 of the second sheet S2 are stacked in a state where they contact each other.

In the present embodiment, the second applicator 32 applies adhesive to the first absorbent layer L1, and then the first absorbent layer L1 and the second absorbent layer L2 are pulled into the stacking roller R, forming the stack S of FIG. 3 (d). The stack S is arranged on the thin paper P conveyed by the stacking roller C3 of FIG. 2.

Thereafter, the thin paper T is folded by the folder 35 of FIG. 1, and then the absorbent body 1 is pressed hard by the pressure contact roller 36, thereby the absorbent body 1 of FIG. 3 (f) formed. In this process, as shown in FIG. 4 (a), the first absorbent layer L1 and the second absorbent layer L2 contact each other and they are sandwiched between the spread layers 21, 21.

Figure 4:
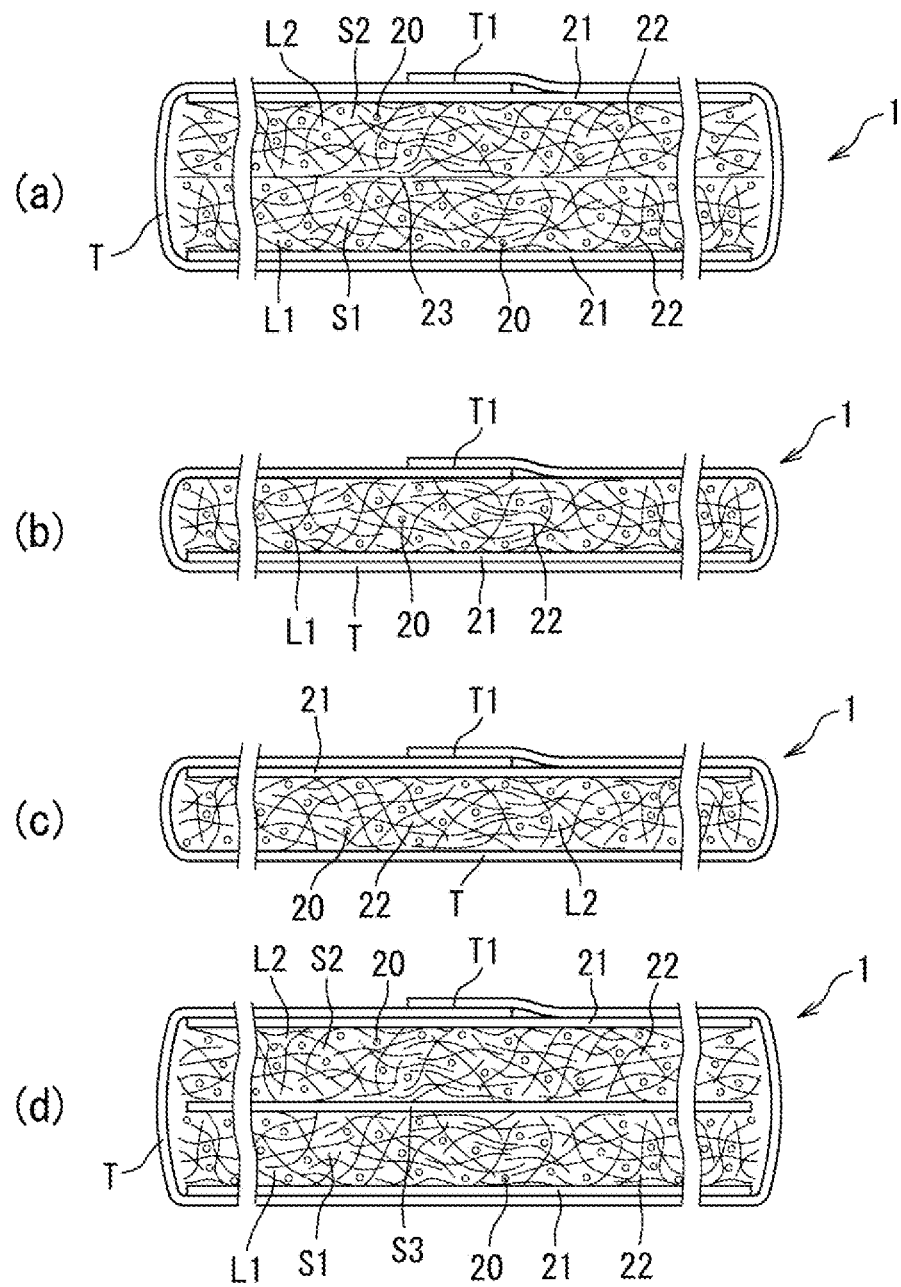
FIG. 4 is an enlarged cross-sectional view showing another structure of an absorbent body.

The present manufacturing apparatus is able to manufacture the absorbent body 1 of FIG. 4 (b) and FIG. 4 (c) in addition to the absorbent body 1 of FIG. 4 (a).

In a case where the absorbent body 1 of FIG. 4 (b) is manufactured, the first unit U1 at the left side of FIG. 1 is operated whereas the second unit U2 at the right side is stopped. In this case, an overlap part T1 of the thin paper T contacts the first absorbent layer L1, and the overlap part T1 and the spread layer 21 are arranged sandwiching the short fiber layer 22 (the first absorbent layer L1).

In a case where the absorbent body 1 of FIG. 4 (c) is formed, the second unit U2 at the right side of FIG. 1 is operated whereas the first unit U1 at the left side is stopped. In this case, the overlap part T1 of FIG. 4 (c) of the thin paper T contacts the spread layer 21.

Now, a case where the absorbent body 1 of FIG. 4 (d) is explained.

The absorbent body 1 of FIG. 4 (d) has a liquid-permeable third sheet S3 between the first sheet S1 and the second sheet S2. The absorbent body 1 is produced by the manufacturing apparatus of FIG. 5.

Figure 5:
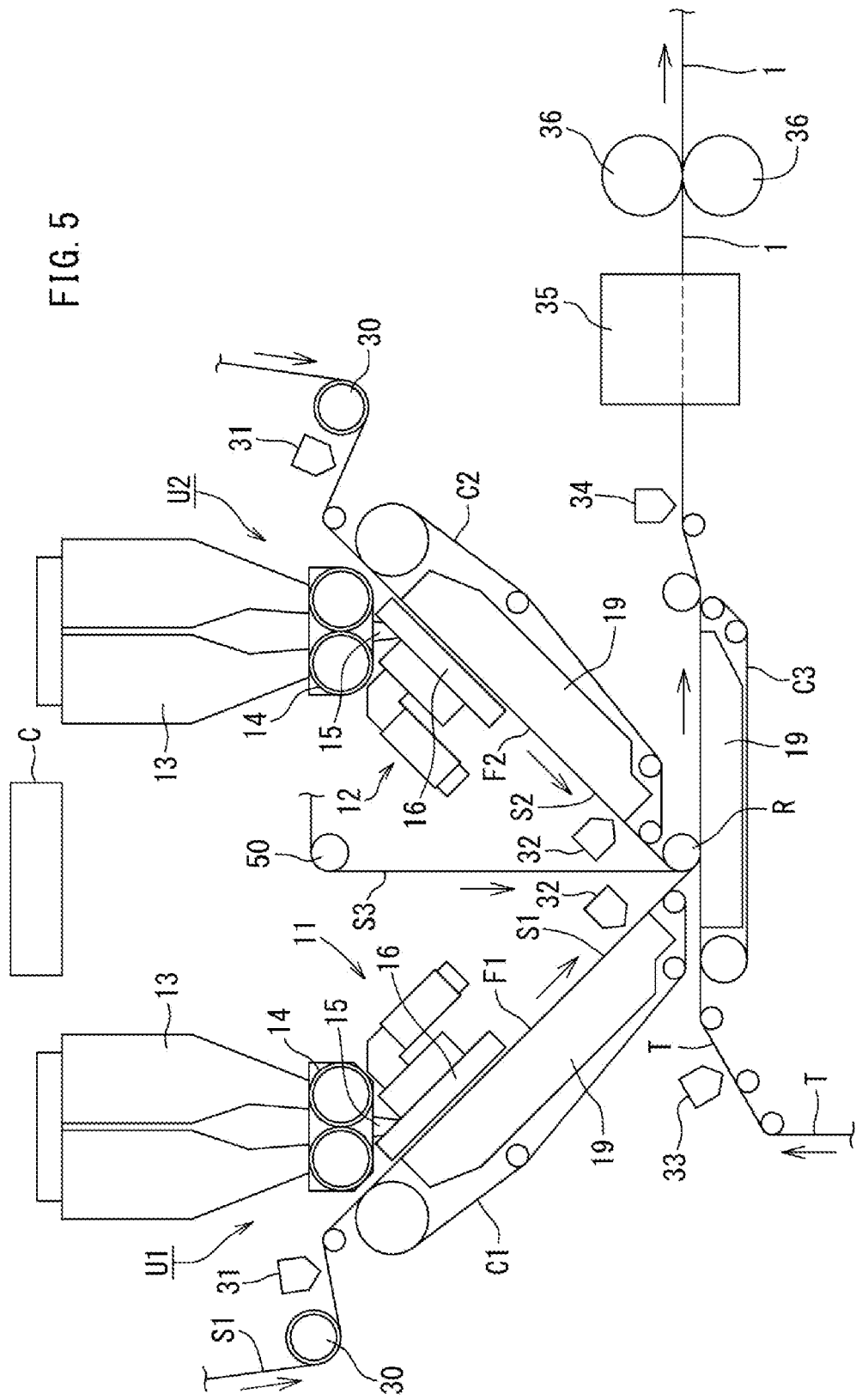
FIG. 5 is a schematic layout diagram showing an embodiment 2 of the manufacturing apparatus.

In FIG. 5, in addition to the manufacturing apparatus of FIG. 1, this embodiment further includes an introduction roller 50 introducing the third sheet S3 into the stacking roller R. The third sheet S3 is introduced between the first sheet S1 and the second sheet S2.

Preferably, the third sheet S3 is a sheet having diffusibility as the spread layer 21 of the first and second sheets S1, S2.

Figure 6:
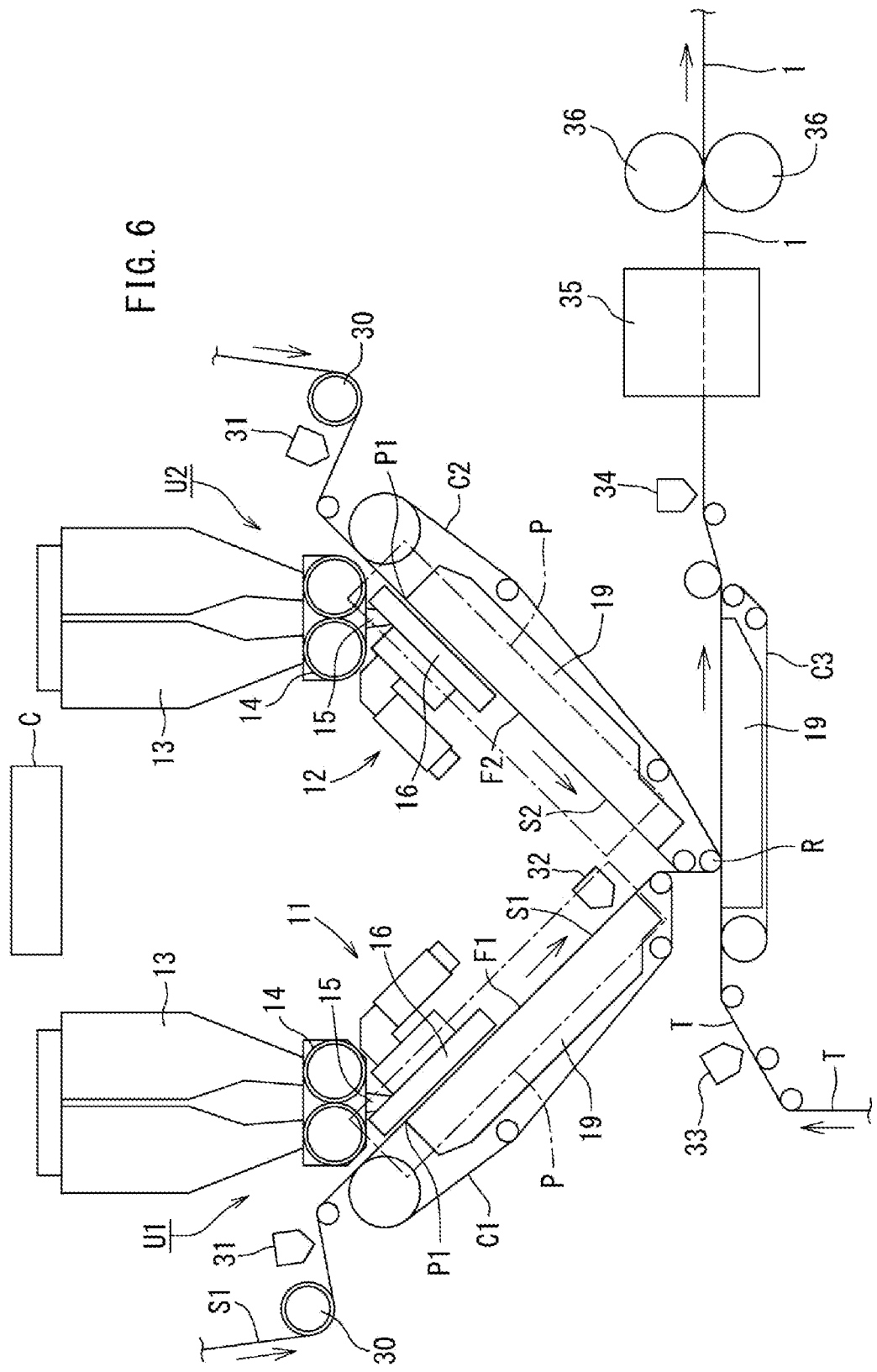
FIG. 6 is a layout diagram showing an embodiment 3 of the manufacturing apparatus.

Now, the manufacturing apparatus of the embodiment 3 in FIG. 6 is explained.

The manufacturing apparatus of FIG. 6 is closely similar to that of the embodiment 1 in FIG. 1. Thus, different parts from the embodiment 1 are mainly explained.

In FIG. 6, negative pressure cases 19 are provided with respective first and second conveyors C1, C2, and may be set to suck air in an area downstream from a point P1 around where the granular powder 20 (FIG. 2) drops. This arrangement prevents the granular powder 20 from scattered by air flow generated between each distribution device 11, 12 and the corresponding conveyor.

Also, scatter-prevention boards P, P may be provided on opposite sides of each conveyor C1, C2 so as to extend along the flow direction of the first and second conveyors C1, C2. The scatter-prevention board P prevents air flow from generated in directions other than the flow direction of the conveyors C1, C2, and thus is useful in preventing scatter of the granular powder 20.

As in this embodiment, the stacking roller R may configure a part of the first conveyor C1 or the second conveyor C2. In this embodiment, the lower-end roller of the second conveyor C2 configures the stacking roller R.

In a case where a diameter of the stacking roller R is large as in FIG. 1, the granular powder 20 (FIG. 2) may scatter near the stacking roller R. With a small diameter of the stacking roller R as in FIG. 6, it is likely to prevent scatter of the granular powder 20.

While a preferred embodiment has been described above with reference to the drawings, various obvious changes and modifications will readily occur to those skilled in the art upon reading the present specification.

For example, if a liquid-permeable non-woven fabric sheet having a fluff-up layer is employed, the fluff-up roller will not need to be provided.

If a pair of nip rollers is employed as the stacking roller R, the first unit U1 and the second unit U2 will be arranged in completely symmetry.

Thus, such changes and modifications shall fall within the scope of the present invention as defined by the appended claims.

INDUSTRIAL APPLICABILITY

The present invention is used in manufacturing various absorbent bodies like disposable underwear and diapers.

REFERENCE SIGNS LIST

1: Absorbent body 11: First distribution device 12: Second distribution device 13: Hopper 14: Meter 15: Guider 16: Distribution case 19: Negative pressure case 20: Granular powder (Powder and granular material) 21: Spread layer 22: Short fiber layer 23: Adhesion layer 30: Fluff-up roller 31-34: Applicator 35: Folder 36: Pressure contact roller 50: Introduction part C1: First conveyor C2: Second conveyor C3: Stacking conveyor F1: First slope surface F2: Second slope surface L1: First absorbent layer L2: Second absorbent layer S: Stack S1: First sheet S2: Second sheet S3: Third sheet T: Thin paper T1: Overlap part U1: First unit U2: Second unit C: Controller P: Scatter-prevention board P1: Point R: Stacking roller

The invention claimed is:

1. A manufacturing apparatus for an absorbent body comprising:
a first conveyor that conveys an air-permeable first sheet while sucking the first sheet along a flat first slope surface;
a second conveyor that conveys an air-permeable second sheet while sucking the second sheet along a flat second slope surface having a slope opposite to the first slope surface;
a first distribution device that forms a first absorbent layer in the first sheet by distributing absorbent powder on an upper surface of the first sheet being conveyed along the first slope surface;
a second distribution device that forms a second absorbent layer in the second sheet by distributing absorbent powder on an upper surface of the second sheet being conveyed along the second slope surface;
a stacking part that stacks the first sheet conveyed by the first conveyor and the second sheet conveyed by the second conveyor in such a manner as to cause the first absorbent layer of the first sheet and the second absorbent layer of the second sheet to face each other; and
a stacking conveyor, on which a paper being fed, that conveys the first and second sheets and the paper in a state where the paper is disposed under a stack of the first and second sheets stacked together,
the stacking part being a stacking roller that rolls in the first sheet conveyed by the first conveyor and the second sheet conveyed by the second conveyor and stacks the first sheet and the second sheet on each other, and
the stacking conveyor contacting the stacking roller with the stack and the paper therebetween.

2. The manufacturing apparatus for an absorbent body according to claim 1, wherein
the first conveyor, the second conveyor, and the stacking roller are arranged in such a manner that the upper surfaces of the first and second sheets conveyed by the first conveyor, the second conveyor, and the stacking roller form a V-shape valley.

3. The manufacturing apparatus for an absorbent body according to claim 1, further comprising:
an introduction part that introduces a liquid-permeable third sheet to be interposed between the first sheet and the second sheet into the stacking roller.

4. The manufacturing apparatus for an absorbent body according to claim 1, further comprising:
a controller that selectively controls operation of at least one of a first unit including the first conveyor and the first distribution device and a second unit including the second conveyor and the second distribution device.

5. A manufacturing method for an absorbent body using the manufacturing apparatus for an absorbent body according to claim 1, comprising:
a step of conveying the first sheet toward the stacking roller while sucking the first sheet along the flat first slope surface of the first conveyor;
a step of conveying the second sheet toward the stacking roller while sucking the second sheet along the flat second slope surface of the second conveyor;
a step of distributing the absorbent powder on the upper surfaces of the first sheet extending along the first slope surface;
a step of distributing the absorbent powder on the upper surfaces of the second sheet extending along the second slope surface;
a step of forming the first absorbent layer by supporting the distributed powder on the first sheet;
a step of forming the second absorbent layer by supporting the distributed powder on the second sheet;

a step of stacking the first sheet and the second sheet in such a manner as to cause the first absorbent layer and the second absorbent layer to face each other at the stacking roller; and a step of feeding the paper to the stacking conveyor and conveying the first and second sheets and the paper in a state where the paper is disposed under the stack of the first and second sheets stacked together and the stacking conveyor contacts the stacking roller with the stack and the paper therebetween.

* * * * *